United States Patent [19]

Saunders et al.

[11] 4,153,428
[45] May 8, 1979

[54] PREPURIFICATION OF TOLUENE DEALKYLATION EFFLUENT GAS

[75] Inventors: John B. Saunders, Tonawanda; James S. Davis, North Tonawanda, both of N.Y.

[73] Assignee: Union Carbide Corporation, New York, N.Y.

[21] Appl. No.: 829,060

[22] Filed: Aug. 30, 1977

[51] Int. Cl.² .............................................. B01D 53/04
[52] U.S. Cl. ............................................ 55/26; 55/33;
55/62; 55/73; 55/74; 55/75
[58] Field of Search ................... 55/33, 62, 73, 75, 25, 55/26, 74

[56] References Cited

U.S. PATENT DOCUMENTS

| | | | |
|---|---|---|---|
| 3,102,013 | 8/1963 | Skarstrom | 55/62 X |
| 3,109,722 | 11/1963 | Dow | 55/33 X |
| 3,149,934 | 9/1964 | Martin | 55/62 X |
| 3,150,942 | 9/1964 | Vasan | 55/33 X |
| 3,237,379 | 3/1966 | Kant et al. | 55/62 X |
| 3,306,841 | 2/1967 | Ward | 55/62 X |
| 3,359,744 | 12/1967 | Bolez et al. | 62/18 X |
| 3,365,859 | 1/1968 | Sandberg | 55/62 X |
| 3,375,674 | 4/1968 | Becker | 62/18 X |
| 3,554,904 | 1/1971 | Humphries | 62/18 X |
| 3,713,272 | 1/1973 | Barrere, Jr. et al. | 55/33 |
| 3,735,600 | 5/1973 | Dowdell et al. | 62/18 X |
| 3,841,058 | 10/1974 | Templeman | 55/33 |

*Primary Examiner*—Robert H. Spitzer
*Attorney, Agent, or Firm*—Steven J. Hultquist

[57] ABSTRACT

A process for separation of water and cyclic hydrocarbons from a gas mixture containing hydrogen, methane, water and cyclic hydrocarbons. An adsorption zone is provided including two adsorbent beds connected in series, one of the beds containing an adsorbent selective for cyclic hydrocarbons and the other bed containing an adsorbent selective for water. Following the passage of gas mixture through the beds, the bed containing cyclic hydrocarbon-selective adsorbent is regenerated with hydrogen-rich purge gas and the bed containing water-selective adsorbent is regenerated with aliphatic hydrocarbon-rich purge gas.

19 Claims, 8 Drawing Figures

PREPURIFICATION OF TOLUENE DEALKYLATION EFFLUENT GAS

BACKGROUND OF THE INVENTION

1. Field of the Invention

This invention relates to a process for separation of water and cyclic hydrocarbons from a gas mixture containing hydrogen, methane, water and cyclic hydrocarbons, such as may be usefully employed for prepurification of effluent gas from a toluene dealkylation process prior to cryogenic separation of the gas mixture.

2. Description of the Prior Art

In a typical toluene dealkylation (TDA) process, a toluene feed stock is mixed with a compressed stream of excess high purity hydrogen and heated to high temperature. The resulting gaseous mixture is then reacted at high temperatures and generally high pressures, either with or without catalysis, to produce an effluent gas containing benzene, methane and unreacted hydrogen and toluene.

Regardless of whether or not catalysis is employed, the method of recovery and purification of the effluent gas from the TDA process is reasonably standard. The effluent gas from the TDA process is initially cooled, first by heat exchange with the feed stream to the toluene dealkylation process and then by supplemental refrigeration, normally a cooling water stream. The resultant two-phase gas mixture thus produced is then phase separated at about 100° F. to yield a benzene-rich liquid and a methane- and hydrogen-containing vapor. The benzene-rich liquid is processed in a recovery and purification system, for upgrading the benzene purity of the liquid. The methane- and hydrogen-containing vapor is concurrently processed to reject methane and return a hydrogen stream to the toluene dealkylation process.

The methane rejection-hydrogen recovery process just mentioned has conventionally involved cryogenic processing of the methane- and hydrogen-containing vapor. The major advantages of cryogenic processes include extremely low energy requirements and relatively low investment costs as compared to other competitive processes, such as absorption systems. The utilization of a cryogenic process, however, requires careful preparation and purification of the feed vapor to remove freezable components. In addition to water (and in many cases hydrogen sulfide), the feed gas mixture for the cryogenic process from the crude benzene separation step is saturated with benzene and toluene. Due to the high freezing point of benzene, plus 42° F., benzene must be removed from the gas mixture along with water and any other contaminants prior to processing in the cryogenic system. The prior art approach to such benzene removal has involved a toluene wash process.

In the conventional toluene wash prepurification process, feed gas mixture for the cryogenic unit, which comprises the vapor fraction from the crude benzene separation described above, is countercurrently flowed against a high purity toluene wash liquid in a gas-liquid contacting column. An impure toluene bottoms liquid is recovered from the column which then augments the feedstock for the toluene dealkylation process, while the overhead vapor recovered from the column, which is saturated with toluene instead of benzene, passes to the cryogenic unit. Since the freezing point of toluene is minus 139° F., it does not pose as severe a threat to the operation of the cryogenic system as does benzene. Most of the toluene can be removed by condensation after an initial cooling step in the cryogenic system; concomittantly, a substantial portion of the water is also removed from the gas mixture. The uncondensed vapor from which condensed toluene has been removed is then passed through an adsorbent dryer prior to further cryogenic processing. In conventional practice, two adsorption beds are provided for drying (residual water removal) so that while one is processing feed gas mixture, the other is being regenerated at lower pressure with a heated portion of the methane rejected in the cryogenic system.

Although the above-described toluene washing operation has been successfully practiced in conjunction with cryogenic treatment of toluene dealkylation effluent gas, it suffers from several potential disadvantages. First of all, to maintain suitable benzene removal, the toluene wash liquid must be very pure, typically containing no more than 2.0% benzene by volume. Since the toluene feed purity specifications for a normal toluene dealkylation process may be as low as 90%, with benzene the major impurity, high purity toluene may not be available in the process system, and auxiliary equipment may be required to produce such a stream. Secondly, even though a substantial quantity of benzene can be removed from the toluene dealkylation effluent gas by toluene washing, there may still be a problem with residual benzene freezing in the heat exchangers of the cryogenic processing system. This is because benzene cannot be removed in the dryers of the adsorption zone, inasmuch as conventional dryers utilize a molecular sieve adsorbent which will not remove a significant quantity of aromatics.

As an alternative to the toluene washing process, it is known to employ an adsorption system for treatment of the effluent gas from the toluene dealkylation unit. Such an adsorption system replaces the toluene wash column, and associated equipment and the adsorbent dryers of the toluene wash system. As a result, the adsorption system exhibits a high potential for economic savings. Such an adsorption system consists of at least two compound adsorbent beds, each containing two adsorbent zones, arranged in parallel flow relationship, such that while one bed is processing the toluene dealkylation effluent gas mixture, the other bed is being regenerated for subsequent gas mixture processing. Typically, the first zone in the compound adsorbent bed contains silica gel adsorbent for aromatics removal while the second zone contains molecular sieve adsorbent for water removal.

In operation of the adsorption system, the methane- and hydrogen-containing vapor phase recovered in the aforementioned crude benzene separation operation is cooled with refrigeration to a temperature in the vicinity of 40° F., phase separated at a temperature as close as possible to the freezing point of benzene and the resulting gas phase is alternately passed through the on-stream adsorbent bed in the adsorption system. Following the adsorption step, the adsorbate-loaded adsorbent bed is thermally regenerated by countercurrently passing a heated portion of the product hydrogen stream from the cryogenic process therethrough. This regeneration stream can then be recycled directly to the toluene dealkylation unit as a portion of the hydrogen requirement therefor, or, alternatively, this stream may be cooled prior to recycling to condense a portion of its aromatic constituents.

Although the adsorption system may, in many cases, provide a suitable replacement for the toluene wash system, the former is plagued by several potential disadvantages. For example, in addition to water, methane, hydrogen and aromatics, the effluent gas mixture from a toluene dealkylation process may also contain appreciable amounts of hydrogen sulfide. Hydrogen sulfide can appear in the toluene dealkylation process effluent gas mixture from primarily two sources. First, sulfur compounds may be present in the make-up hydrogen feed stream for the toluene dealkylation unit; the toluene dealkylation reactor generally converts all such compounds to hydrogen sulfide. Since, when catalysis is used, the toluene dealkylation process is sensitive, in varying degrees, to the presence of hydrogen sulfide, such catalytic processes may be provided with a make-up gas pretreatment step to minimize the source of hydrogen sulfide. Second, carbonyl sulfide may be purposely added to the feed gas streams for a thermal toluene dealkylation reactor as a corrosion inhibitor. Subsequently, in the toluene dealkylation reactor, the carbonyl sulfide is converted to hydrogen sulfide.

Any hydrogen sulfide in the toluene dealkylation effluent gas (vapor fraction recovered from the crude benzene separation operation) will be primarily coadsorbed with water in the adsorption system. This hydrogen sulfide is subsequently recycled with the aromatics to the toluene dealkylation unit after regeneration of the adsorbent beds, by hot hydrogen purging thereof. The recycled hydrogen sulfide will add to any sulfur compounds present in the toluene dealkylation reactor feed gas and increase the dealkylation loop's overall sulfur content. Repetitive adsorption-desorption of hydrogen sulfide in the adsorption system may continue for a lengthy period as a result of the adsorbent's ability to co-adsorb fairly large quantities of hydrogen sulfide. As a result, hydrogen sulfide will build up until a sufficient quantity is present in the dealkylation loop to either poison the dealkylation reactor catalyst, in the case of a catalytic toluene dealkylation system, or else saturate the adsorbent zone and subsequently break through in sufficient quantities to freeze the cryogenic system.

It is also known that a heated stream of rejected methane from the cryogenic system can also be used as the regeneration gas for regeneration of the adsorbent beds in the adsorption system. In this manner, any hydrogen sulfide which is coadsorbed with water will be rejected to fuel with the methane-rich gas, thereby preventing buildup of hydrogen sulfide in the dealkylation loop (of recycled hydrogen-rich gas). Nonetheless, such an approach results in significant aromatics losses via the rejected fuel gas purging stream (methane-rich gas). Recovery of aromatics from the adsorption system regeneration gas requires the added expense of an additional refrigeration and recovery step. In addition, only about 50% of the adsorbed aromatics can be easily recovered, resulting in only 85% to 91% overall recovery of aromatics from the gaseous phase obtained from the crude benzene separation, as compared to 99% recovery levels typical for the toluene wash system. However, the adsorption system still offers a simpler and more reliable pretreatment than the conventional toluene wash system.

In addition to processing the toluene dealkylation effluent gas mixture for the recovery of recycle hydrogen, the cryogenic system can also be employed to purify the hydrogen make-up stream for the dealkylation unit. This integrated operation is in many cases more economical than separate treatment. Sources of hydrogen for toluene dealkylation include, among others, catalytic reforming, ethylene plant off-gas and coal gasification; such processes produce gases containing water, carbon dioxide, carbon monoxide and light alkyl hydrocarbons in addition to the desired hydrogen. The cryogenic system can safely handle the carbon monoxide and light hydrocarbons, but before processing such a stream, the water content, carbon dioxide content and other potential contaminants such as hydrogen sulfide must be removed therefrom. In convention practice, this is normally accomplished by passing the make-up hydrogen stream through a bed of adsorbent material which has an affinity for water, carbon dioxide and the other contaminants, as for example, molecular sieve. In this manner the make-up hydrogen stream may be conveniently processed, together with the toluene dealkylation effluent gas mixture (vapor phase recovered from the crude benzene separation), in the adsorption system. However, as is the case when processing an effluent gas mixture stream containing hydrogen sulfide, regeneration of the adsorption system with a hot stream of recycled hydrogen gas derived from the cryogenic system allows the concentration of impurities, e.g., water, carbon dioxide and the other contaminants in the make-up hydrogen stream, to build up in the dealkylation loop. Eventually, the adsorption unit will become saturated with these impurities and they will break through the adsorption system in quantities sufficient to freeze the cryogenic system. To prevent such occurrence, the adsorbent beds in the adsorption system must be regenerated in the same manner as when treating a hydrogen sulfide-containing effluent gas mixture, i.e., regeneration with hot fuel gas (rejected methane) from the cryogenic system, even though such regeneration leads to low aromatics recovery. Another problem associated with processing the toluene dealkylation effluent gas mixture and hydrogen make-up streams together in the adsorption system in that the presence of higher aliphatic hydrocarbons in the hydrogen make-up stream will tend to lower the loading of aromatic constituents such as benzene on the adsorbent in the beds of the adsorption system, thereby reducing the recovery of such aromatic constituents from the toluene dealkylation effluent gas mixture.

In addition to the above-mentioned disadvantages, mixing the hydrogen make-up stream with the toluene dealkylation effluent gas stream for concurrent introduction to the adsorption system results in an increased adsorbent requirement in the adsorption system for removal of aromatic constituents from the combined gas stream. In order to carry out the concurrent introduction of toluene dealkylation effluent gas and hydrogen make-up gas to the adsorption system in the toluene dealkylation system, the hydrogen make-up stream could merge with the toluene dealkylation effluent gas either prior to or subsequent to the low temperature benzene separation, which is conventionally conducted at 45° to 50° F. In the first case, where the gas streams are merged prior to the benzene separation step a greater quantity of gas is recovered from the low temperature benzene separation, but since any benzene in the vapor phase is still at its appropriate saturation pressure, a larger absolute quantity of benzene is present in the vapor phase. Thus, a larger quantity of adsorbent is required than is necessary when processing only the effluent gas stream from the toluene dealkylation unit. In the second instance, the addition of hydrogen make-up gas to the vapor phase recovered from the low temperature benzene separation dilutes the benzene concentration of the separated gas and may necessitate increased adsorbent requirements, as a result of the reduction in benzene partial pressure.

Accordingly, it is an object of the present invention to provide an improved process for the separation of water and cyclic hydrocarbons from a gas mixture containing hydrogen, methane and the water and cyclic hydrocarbons.

It is a further object of the present invention to provide a method for preventing undesirable gaseous components such as $H_2S$ and $CO_2$ from fouling behavior in the toluene dealkylation system, as a result of their build-up in the dealkylation loop, and from causing freeze-up of the cryogenic system, while simultaneously obtaining high recovery of cyclic hydrocarbon (aromatic) constituents from the toluene dealkylation effluent gas mixture.

Other objects and advantages of the present invention will be apparent from the ensuing disclosure and appended claims.

SUMMARY OF THE INVENTION

This invention relates to a process for separation of water and cyclic hydrocarbons from a gas mixture containing hydrogen, methane and said water and cyclic hydrocarbons.

In the process of the invention, an adsorption zone is provided including two adsorbent beds connected in series, one of the beds containing an adsorbent selective for cyclic hydrocarbons and the other bed containing an adsorbent selective for water. The gas mixture is sequentially passed through the beds for preferential adsorption therein of cyclic hydrocarbons and water, and cyclic hydrocarbon- and water-depleted gas mixture is discharged from the adsorption zone. A hydrogen-rich gas substantially free of cyclic hydrocarbons is heated as purge gas and passed through a bed containing cyclic hydrocarbon-selective adsorbent having previously been at least partially loaded with cyclic hydrocarbons by passage of the gas mixture therethrough, thereby desorbing substantially all of the cyclic hydrocarbons and discharging cyclic hydrocarbon-containing purge gas therefrom. An aliphatic hydrocarbon-rich gas substantially free of water is heated as purge gas and passed through a bed containing water-selective adsorbent having previously been at least partially loaded with water by passage of the gas mixture therethrough, thereby desorbing substantially all of the water and discharging water-containing purge gas therefrom. The desorbed adsorbent beds are then cooled, for subsequent passage of the gas mixture therethrough in the manner previously described.

In a preferred embodiment of the invention, the cyclic hydrocarbon- and water-depleted gas mixture discharged from the adsorption zone is separated into hydrogen-rich gas and methane-rich gas, with the hydrogen-rich gas being employed as the aforementioned purge gas for the bed containing cyclic hydrocarbon-selective adsorbent, and the methane-rich gas being employed as the aliphatic hydrocarbon-rich purge gas for the bed containing water-selective adsorbent.

As an important advantage of the use of the adsorption process of the present invention, the low temperature benzene separation operation in the toluene dealkylation system, wherein benzene is condensed and separated from cooled toluene dealkylation effluent gas mixture, may be carried out at higher temperatures than conventionally practiced, thereby effecting a savings in system cooling refrigeration requirements. This advantage is due to the fact that the adsorption process of the present invention is capable of providing high recovery of aromatic hydrocarbon constituents, including benzene, which are recycled back to the toluene dealkylation reactor in the hydrogen-rich purge gas used to regenerate the adsorbent bed containing cyclic hydrocarbon-selective adsorbent. Thus, the required removal level for benzene in the low temperature benzene separation step is reduced, with corresponding reduction in the degree of gas mixture cooling associated with such separation step. In a toluene dealkylation system employing the adsorption process of the present invention, the low temperature benzene separation operation may be carried out at temperatures as high as 100° F., although lower temperatures, above the freezing point of benzene in the gas mixture, are correspondingly more favorable to the adsorption process, tending to yield longer adsorption step times due to the resulting smaller quantity of benzene in the vapor phase of the gas mixture. By contrast, in prior art toluene dealkylation systems, the low temperature benzene separation operation must employ temperatures on the order of between 45° F. and 55° F. and generally as close to the freezing point of benzene as possible, in order to insure adequate recovery of benzene from the toluene dealkylation effluent gas mixture.

As used herein, the term "cryogenic unit" and "cryogenic system" refers to the complete set of heat exchangers, phase separators, expansion valves and piping employed for low temperature separation of gas mixture containing hydrogen and methane to produce a hydrogen-rich gas and methane-rich gas.

As used herein, the term "cyclic hydrocarbons" refers to aromatic compounds such as benzene, toluene, xylene and naphthalene as well as non-aromatic compounds such as cyclo-hexane.

DESCRIPTION OF THE PREFERRED EMBODIMENTS

Figure 1:
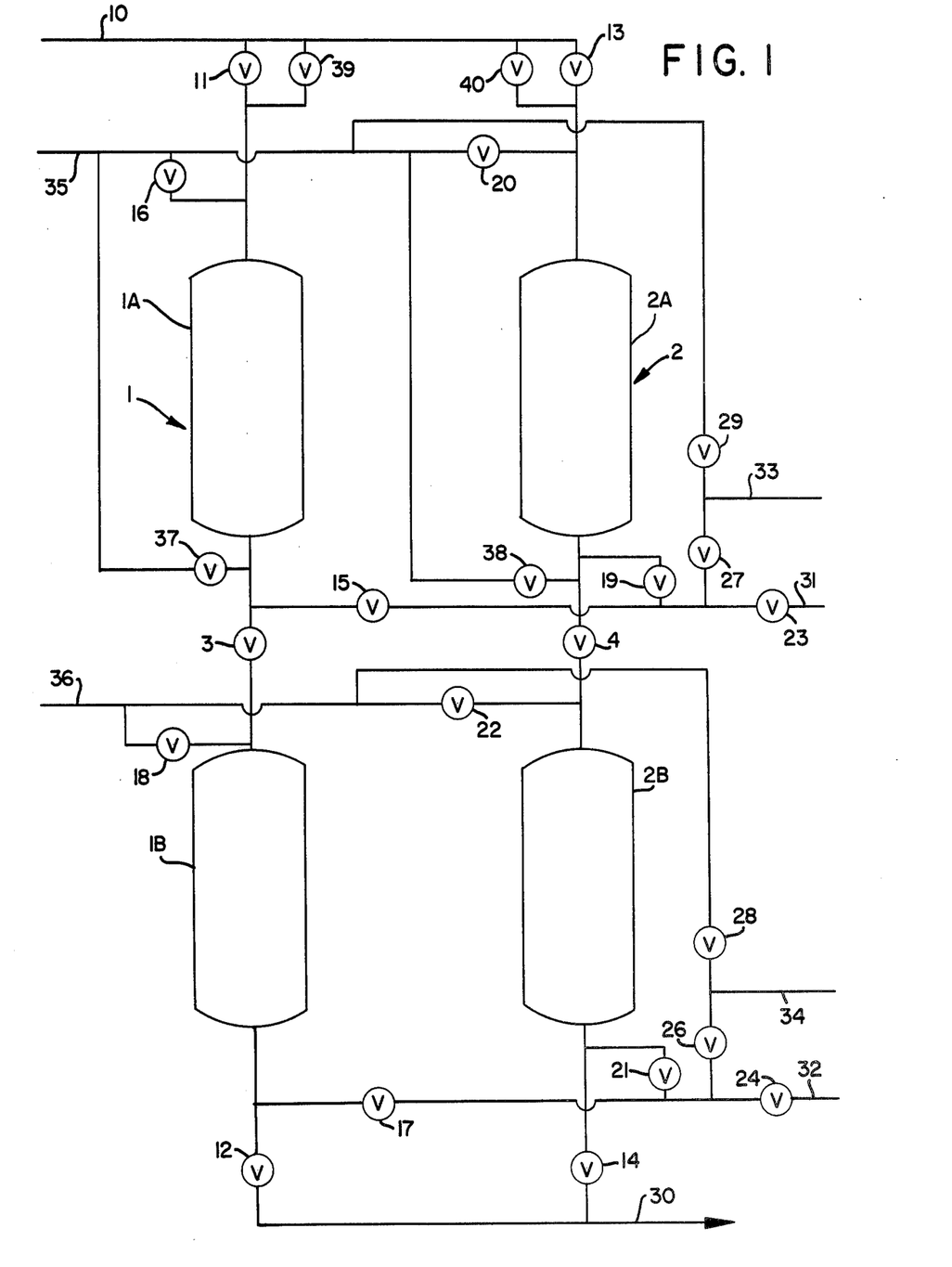
FIG. 1 is a schematic flow sheet of an adsorption system suitable for the practice of the instant invention, comprising two adsorbent beds connected in series in each of two adsorbent zones.

The present invention is directed to a process for separation of water and cyclic hydrocarbons from a gas mixture containing hydrogen, methane, water and cyclic hydrocarbons, such as may be usefully employed for a prepurification of effluent gas mixture from a toluene dealkylation process. The invention has particular utility in the pretreatment of a gas mixture containing both water and other relatively high-freezing components, such as hydrogen sulfide. As discussed earlier herein, the toluene dealkylation effluent gas mixture treatment processes employed by the prior art are deficient with respect to processing of such a stream. FIG. 1 is a schematic flow sheet of an adsorption system such as may be usefully employed for prepurification of a gas mixture recovered from the low temperature benzene separation step in a toluene dealkylation process containing hydrogen, methane, water, benzene and substantial amounts of hydrogen sulfide.

In the FIG. 1 embodiment, two adsorption zones 1 and 2 are provided, each including two adsorbent beds connected in series, one of the beds containing an adsorbent selective for cyclic hydrocarbons and the other bed containing an adsorbent selective for water. In the following description, adsorption zone 1 consisting of adsorbent beds 1A and 1B is on the adsorption portion of the cycle and the adsorption zone 2, consisting of adsorbent beds 2A and 2B, is on the desorption portion of the cycle. This two adsorption zone system contemplates a continuous cyclic process wherein one zone is on the adsorption portion of the cycle and the other zone is on the regeneration portion of the cycle at all times.

In operation of the FIG. 1 embodiment, gas mixture from, for example, the low temperature benzene separation step in a toluene dealkylation process, containing hydrogen, methane, benzene, water and hydrogen sulfide, is passed through conduit 10 to the adsorption system. As described above, the adsorption system consists of two parallel adsorption zones 1 and 2. Each zone consists of two serially staged adsorbent beds. Adsorption zone 1 consists of adsorbent beds 1A and 1B along with the necessary inter-bed piping, while the adsorption zone 2 consists of adsorbent beds 2A and 2B. In this embodiment, the first adsorbent bed, i.e., beds 1A and 2A, of each adsorption zone contains an adsorbent having a high selectivity for water and hydrogen sulfide relative to the other stream components, while the second adsorbent bed, i.e., beds 1B and 2B, of each adsorption zone is filled with an adsorbent having a high selectivity for cyclic hydrocarbons (aromatics) relative to the remaining stream constituents. By way of example, the adsorbent beds 1A and 2A may contain an adsorbent selective for water such as molecular sieve, as for example 4A, 5A or 13X. Adsorbent beds 1B and 2B, containing adsorbent selective for cyclic hydrocarbon, may for example contain silica gel or activated carbon.

In some instances in the broad practice of the present invention, it may be desirable to dispose the bed containing cyclic hydrocarbon-selective adsorbent first in series, upstream of the bed containing water-selective adsorbent. Such arrangement is in many cases preferred since the small amount of aromatic (cyclic hydrocarbon) co-adsorption which otherwise occurs in the water removal adsorbent bed causes carbon deposition and gradual degradation of the adsorbent material selective for water. Nonetheless, in the case of a toluene dealkylation process producing an effluent gas containing measurable amounts of hydrogen sulfide, wherein the toluene dealkylation reactor is of a catalytic character and the hydrogen-rich regeneration purge gas flowed through the adsorbent bed containing adsorbent selective for cyclic hydrocarbons is thereafter recycled to the toluene dealkylation reactor, it is desirable to remove any hydrogen sulfide prior to removal of cyclic hydrocarbons so as to minimize any co-adsorption of hydrogen sulfide with the cyclic hydrocarbons. This is due to the fact that the co-adsorbed hydrogen sulfide would be recycled with the cyclic hydrocarbons, in the hydrogen-rich purge gas, to the toluene dealkylation unit and would cause catalyst deactivation therein.

In the operation of the FIG. 1 adsorption system, gas mixture enters the system through conduit 10, passes respectively through open valve 11, bed 1A, containing water selective adsorbent material, open valve 3, bed 1B, containing cyclic hydrocarbon-selective adsorbent material and then is discharged from the adsorption zone 1 through open valve 12 into conduit 30 as purified gas mixture; this discharged gas mixture, depleted in water and cyclic hydrocarbons, may then be passed to a cryogenic unit (not shown) of a toluene dealkylation system. Since the adsorption zone 1 is processing gas mixture, valves 15, 16, 17, 18, 37 and 39, which are associated with the regeneration of adsorption zone 1, are closed. As the feed gas mixture passes through adsorption zone 1, water and hydrogen sulfide are preferentially adsorbed on the water-selective adsorbent material in bed 1A, while the cyclic hydrocarbon constituents generally pass through this bed and then are subsequently adsorbed on the cyclic hydrocarbon selective material in bed 1B. A typical time length for the adsorption step in an illustrative embodiment is about 8 hours.

While the adsorption zone 1 is processing gas mixture, the adsorption zone 2 is on the regeneration portion of the cycle. Regeneration of the adsorption zones is accomplished by flowing appropriate high temperature purge gas streams through the beds in the adsorption zone. Prior to the regeneration portion of the cycle, the adsorption zone 2 is isolated from conduits 10 and 30 by closing valves 13 and 14 respectively. Additionally beds 2A and 2B in adsorption zone 2 are isolated from each other by closing valve 4. This embodiment of the invention features simultaneous regeneration of the cyclic hydrocarbon and water adsorbent beds. In this embodiment, the bed containing cyclic hydrocarbon selective adsorbent is countercurrently purged with hot hydrogen-rich gas, substantially free of cyclic hydrocarbons which is conveniently obtained by heating the hydrogen-rich gas product from the cryogenic unit when the adsorption process is employed in a toluene dealkylation system for prepurification of the effluent gas mixture from the toluene dealkylation reactor. The adsorbent bed containing water selective adsorbent is countercurrently purged with hot aliphatic hydrocarbon-rich gas substantially free of water, which is suitably obtained by heating the methane-rich gas derived from the cryogenic unit in a toluene dealkylation system.

A hydrogen-rich gas is heated (means not shown) as purge gas and enters the system in conduit 34, passes respectively through valves 26 and 21 and then flows through an adsorbent bed 2B, containing adsorbent selective for cyclic hydrocarbons. The heated gas provides the heat of desorption necessary to remove the aromatics (cyclic hydrocarbons) from bed 2B. The cyclic hydrocarbon-laden hydrogen-rich purge gas is then discharged from bed 2B through valve 22 and conduit 36, and is used as recycle hydrogen gas for the toluene dealkylation reactor when the adsorption system is employed in a toluene dealkylation system. Next, the bed 2A is purged with a heated aliphatic hydrocarbon-rich gas substantially free of water. In a toluene dealkylation system, this purge gas may conveniently be derived from the cryogenic unit, which produces methane-rich gas as product. Since in a toluene dealkylation system, the methane-rich purge gas obtained from the cryogenic unit is at a substantially lower pressure than the pressure in beds 2A and 2B at the conclusion of their adsorption step, the pressure in bed 2A must be reduced prior to the hot methane-rich gas purge when using such cryogenic unit as a purge gas source. This accomplished by co-currently depressurizing bed 2A through valve 38 into conduit 35. Once the depressurization is complete, valve 38 is closed and hot methane-rich purge gas substantially free of water enters conduit 33, passes respectively through valves 27 and 19, and then flows through adsorbent bed 2A. Passage of methane-rich gas through bed 2A containing water selective adsorbent having previously been at least partially loaded with water by passage of gas mixture therethrough effects desorption of substantially all of the water therefrom. The water-containing purge gas is then discharged from bed 2A, also containing the desorbed hydrogen sulfide, through valve 20 and conduit 35. By utilizing the methane-rich gas of the cryogenic unit for desorption of this bed, the hydrogen sulfide can be removed from the dealkylation loop with little loss of cyclic hydrocarbons. At the end of the desorption portion of the cycle, beds 2A and 2B of adsorption zone 2 are cooled to substantially the gas mixture processing temperature. Bed 2B can be cooled, for example, by passing cool hydrogen-rich gas through conduit 32, valves 24 and 21 and subsequently removing it from the bed through valve 22 and conduit 36. In similar fashion, bed 2A can be cooled by passing cool methane-rich gas through conduit 31 valves 23 and 19 and discharging the cool gas from the bed through valve 20 and conduit 35. Upon completion of the cooling step, bed 2A is repressurized. This is accomplished by closing valves 19 and 20, and allowing gas mixture to enter bed 2A through valve 40. Once bed 2A has been repressurized, valve 40 is closed.

Alternatively, repressurization of bed 2A could occur prior to the cool purge rather than after the cool purge, as described above. In the alternative mode, after repressurization with feed gas, bed 2A could be cooled by hydrogen-rich gas by opening valve 4 during the cooling of bed 2B. Nonetheless, for such repressurization scheme additional piping and valving would be needed to pass hydrogen-rich gas from conduit 35 to conduit 36.

After adsorption zones 1 and 2 each finish their respective adsorption-regeneration portions of the cycle, the cycle is continued by placing zone 1 on regeneration and zone 2 on adsorption. Valves 11, 3 and 12, which are associated with the adsorption portion of the cycle for zone 1, are closed, while valves 15, 16, 17, 18, 37 and 39 are open as required. Similarly, valves 19, 20, 21, 22, 38 and 40, which are associated with the regeneration portion of the cycle for adsorption zone 2, remain closed, while valves 13, 4 and 14 are opened.

Subsequently, the regeneration of adsorption zone 1 and adsorption in adsorption zone 2 proceeds in the manner described in connection with the preceding portions of the cycle. Hydrogen-rich gas can be bypassed through conduit 34 and valve 28 and methane-rich gas can be bypassed through conduit 33 and valve 29 when not required for regeneration.

In the broad practice of the present invention, the aliphatic hydrocarbon-rich gas, as for example substantially pure methane, ethane or propane gas, and the hydrogen-rich gas, as used for purging the respective adsorbent beds, may be derived from any suitable source and are not limited in such respect to the hydrogen and methane streams from a cryogenic unit in a toluene dealkylation process, although a cryogenic unit source is preferred when the adsorption process of the present invention is used for prepurification of toluene dealkylation effluent gas mixture subsequently passed to such a cryogenic unit, for separation of the effluent gas mixture into hydrogen-rich gas and methane-rich gas.

Figure 2:
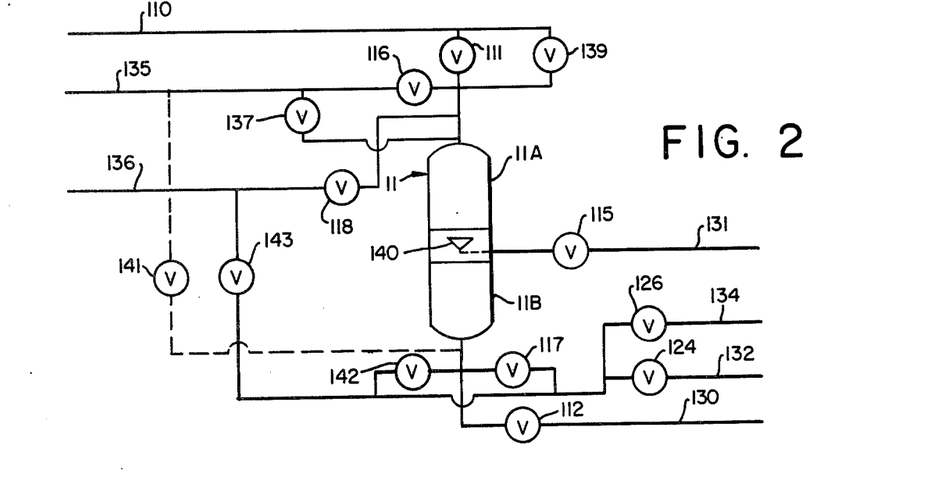
FIG. 2 is a schematic flow sheet of another adsorption system such as may be suitably employed in the practice of the present invention, comprising a single adsorption zone including two adsorbent beds connected in series.

The method of this invention can also be practiced with an adsorption zone which combines the two adsorbend beds into a single vessel as shown in the FIG. 2 schematic drawing. As shown in FIG. 2, a special fluid distribution device 140, which may in practice comprise a sparger of a type well known in the art, is necessary between zones 11A and 11B for regenerating the bed 11A with aliphatic hydrocarbon-rich gas. In operation, gas mixture containing hydrogen, methane, water, hydrogen sulfide and cyclic hydrocarbons, enters through conduit 110, passes respectively through valve 111 and beds 11A and 11B, and is discharged from the adsorption zone through valves 112 and conduit 130 as prepurified gas mixture which may then be passed to a cryogenic unit as for example when the adsorption zone is employed in a toluene dealkylation process system. This adsorption step may continue for approximately 8 hours. While the adsorption zone 11 is on the adsorption portion of the cycle, valves 115, 116, 117, 118, 137 and 139, which are employed in the regeneration of the adsorption zone 11, are closed.

At the completion of the adsorption step, the flow of gas mixture through adsorption zone 11 is terminated by closure of valves 111 and 112, thereby isolating the adsorption zone 11 from further gas mixture processing. The adsorption zone 11 is initially depressurized by opening valve 137, thereby allowing the contents of the adsorption zone 11 to slowly bleed into the (fuel rejection) conduit 135. As opposed to the previous embodiment of the invention described in connection with FIG. 1, in which depressurization is cocurrent, in the process associated with FIG. 2, the depressurization is countercurrent to the direction of feed gas mixture flow. In the broad practice of the present invention, depressurization of adsorbent beds may be carried out either countercurrently or co-currently. The particular method of depressurization is a matter of choice depending on the characteristics of the given adsorption system and is a function of the relative effects which the particular method of depressurization has on piping and valving requirements and on the adsorption system's overall performance, all of which is well-known to one of ordinary skill in the art. The adsorption zone 11 could be co-currently depressurized simply by opening valve 141 thereby allowing the contents of adsorption zone 1 to slowly bleed into the fuel rejection conduit 135. In normal practice, countercurrent depressurization is favored since this method minimizes the possibility of freezable components entering the cryogenic unit of the toluene dealkylation system.

In contrast to the previously described embodiment of FIG. 1, the depressurization of bed 11A is accompanied by depressurization of bed 11B. Once the depressurization is complete, valve 137 is closed and bed 11A is purged with hot methane-rich gas from the cryogenic system (heating means not shown) which enters through conduit 131 and valve 115 respectively. As indicated earlier, to properly distribute the regeneration purge gas in bed 11A, a flow distribution device 140, of a type well known to those skilled in the art, is employed. Water- and hydrogen sulfide-containing methane-rich purge gas is discharged from bed 11A through valve 116 and conduit 135. After zone 11A has been thoroughly purged with hot methane-rich gas, valves 115 and 116 are closed and adsorption zone 11 is repressurized with feed gas mixture through conduit 110 and valve 139. As an alternative, adsorption zone 11 could be repressurized with hydrogen-rich gas from the cryogenic unit through conduit 132 in valves 124 and 142. Once the repressurization step is complete, valve 139, or alternatively, valve 142, is closed and hot hydrogen-rich gas (heating means not shown) enters adsorption zone 11 through conduit 132, valve 124 and valve 117. This gas passes sequentially though beds 11B and 11A of the adsorption zone 11 for a time sufficient to remove substantially all of the previously adsorbed aromatic components (cyclic hydrocarbons) in bed 11A. The hot aromatics-laden hydrogen-rich gas then is discharged from adsorption zone 11 through valve 118 and conduit 136. At the end of the hot, hydrogen-rich purge step, valve 124 is closed and cool hydrogen-rich gas enters the adsorption zone 11 through conduit 134, and valves 126 and 117, to complete the regeneration of adsorbent beds 11A and 11B for the subsequent processing of feed gas mixture on the adsorption step. By-pass of the hydrogen-rich gas from the cryogenic system is provided through valve 143 during the subsequent adsorption step; thus, this hydrogen-rich gas is recycled directly to the toluene dealkylation reactor during the adsorption step for adsorption zone 11.

Preferably, two adsorption zones similar to the one shown in FIG. 2 are provided, so that one adsorption zone is undergoing the sequential hot methane-hot hydrogen purges of the desorption portion of the cycle while the other adsorption zone is processing feed gas mixture. The FIG. 2 embodiment offers two advantages relative to the FIG. 1 embodiment previously described. First of all, only one vessel contains the two adsorbent beds for a complete adsorption prepurification system. Secondly, fewer automatic valves and less instrumentation would be necessary in the system operating according to the FIG. 2 embodiment, relative that shown in FIG. 1.

It will be noted that in the embodiments previously described above, each adsorption zone includes a bed containing water-selective adsorbent disposed first in the series, upstream of the bed containing cyclic hydrocarbon adsorbent. Such an arrangement is desirable where hydrogen sulfide is present in the feed gas mixture and the toluene dealkylation reactor is catalytic in character and thus sensitive to sulfur compounds in the gas recycled to the toluene dealkylation reactor. Nonetheless, there are several minor disadvantages associated with such an arrangement, as a result of cyclic hydrocarbons co-adsorbing in the water removal bed. First of all, carbon deposition will occur, resulting in the gradual degradation of the water-selective adsorbent material. Secondly, there is an increased adsorbent requirement for water removal because of the aromatics (cyclic hydrocarbons) co-adsorption. Finally, there will be minor losses of cyclic hydrocarbons with the methane (aliphatic hydrocarbon)-rich purge gas discharged from the regenerated water adsorption zone. Thus, when recycled co-adsorbed hydrogen sulfide does not represent a problem, it is generally desirable to deploy the bed containing cyclic hydrocarbon-selective adsorbent first in series, upstream of the bed containing water-selective adsorbent.

Figure 3:
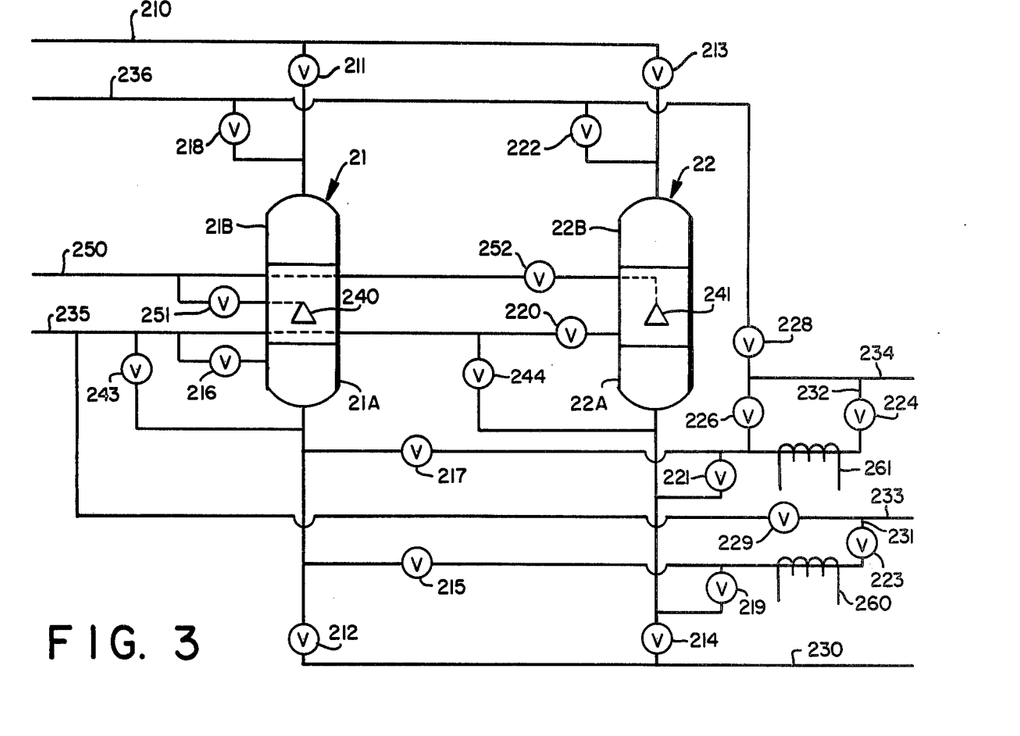
FIG. 3 is a schematic flow sheet of another adsorption system such as may be suitably employed in the practice of the present invention, comprising two adsorption zones each including two adsorbent beds connected in series.

FIG. 3 is a schematic flow sheet of an adsorption system wherein, in each adsorption zone, the bed containing cyclic hydrocarbon-selective adsorbent is disposed first in series, upstream of the bed containing water-selective adsorbent. Such an adsorbent prepurification system may be used to treat not only the vapor phase recovered from the low temperature benzene separation in the toluene dealkylation system, but also the make-up hydrogen stream for the toluene dealkylation system, such as may be obtained for example from a methanator system. A make-up hydrogen stream obtained from a methanator system will typically have a concentration similar to that shown in Table I below.

TABLE I

| COMPOSITION OF METHANATOR OFF-GAS | |
|---|---|
| Component | Mole % |
| $H_2$ | 46.2 |
| $H_2O$ | Saturated |
| $C_2H_6$ | 0.13 |
| $CH_4$ | 53.0 |
| $H_2S$ | 30 PPM |

Such combined treatment, for prepurification not only of the vapor phase recovered from the low temperature benzene separation but also the hydrogen make-up stream for the toluene dealkylation system, is more economical than separate treatment units for each stream.

In operation of the FIG. 3 adsorption system, feed gas mixture from the low temperature benzene separation passes through conduit 210 and open valve 211 into adsorption zone 21. The further description of this embodiment will be based on the adsorption zone 21 being on the adsorption portion of the cycle, while adsorption zone 22 is on the regeneration portion of the cycle. In such mode, valves 215, 216, 217, 218 and 243, which are associated with the regeneration of adsorption zone 21, are closed.

In addition to the feed gas mixture entering through conduit 210, an additional feed stream, comprising the methanator-off gas hydrogen make-up stream for the toluene dealkylation reactor, passes through conduit 250, open valve 251 and gas distribution device 240 and merges with the cyclic hydrocarbon-depleted gas leaving bed 21B. The hydrogen make-up stream could be mixed with the toluene dealkylation unit product stream either prior to or subsequent to the low temperature benzene separation; however, each method will result in increased adsorbent requirements for the cyclic hydrocarbon selective adsorbent bed. In the first case, a greater quantity of gas is required from the low temperature benzene separation — since any benzene in the vapor phase is still at its appropriate saturation pressure, a larger absolute quantity of benzene is present in the vapor phase. Accordingly, a larger quantity of adsorbent is required than is otherwise necessary for an equivalent adsorption time. In the second case, when the hydrogen make-up gas from the methanator is mixed with the toluene dealkylation unit product effluent gas stream subsequent to the low temperature benzene separation, the addition of the methanator off-gas to the vapor phase recovered from the low temperature benzene separation dilutes the benzene concentration in the gas phase and may necessitate increased adsorbent requirements as a result of the reduction in benzene partial pressure in the gas phase.

Returning to FIG. 3, the combined stream of the cyclic hydrocarbon-depleted gas from adsorbent bed 21B and the methanator off-gas from conduit 250 then passes through adsorbent bed 21A containing water selective adsorbent material which removes the water from the gas mixture and the remaining hydrogen sulfide therefrom and is discharged from the adsorption zone through valve 212 and conduit 230 to the cryogenic unit.

While adsorption zone 21 is on the adsorption portion of the cycle, adsorption zone 22 is on regeneration. Prior to the regeneration of beds 22A and 22B of adsorption zone 22, valves 213, 252 and 214, which are associated with the adsorption portion of the cycle for adsorption zone 22, are closed. The regeneration of these zones is carried out in much the same manner as in the FIGS. 1 and 2 embodiments previously described, with hot hydrogen-rich gas being employed to desorb the cyclic hydrocarbons from the cyclic hydrocarbon-selective adsorbent in zone 22B and hot methane-rich gas being employed to desorb the water from the water selective adsorbent in bed 22A along with the co-adsorbed hydrogen sulfide in bed 22A. Initially, adsorption zone 22 is co-currently depressurized through valve 244. Then, valve 244 is closed and bed 22A is purged with hot methane-rich gas from the cryogenic separation system. The methane-rich gas flows through the conduits 233 and 231 and valve 223 and is heated to high temperature by heater 260. The hot methane-rich gas then passes through valve 219, bed 22A containing water-selective adsorbent material and is discharged therefrom through valve 220 into line 235. Upon completion of the hot methane-rich gas purge, valves 219, 220 and 223 are closed and adsorption zone 22 is repressurized with effluent gas mixture from the crude benzene separation through conduit 210 and valve 213.

When the repressurization step is completed, valve 213 is closed and valves 224, 221 and 222 are opened to permit hot hydrogen-rich purge gas to flow consecutively through adsorbent beds 22A and 22B, the latter containing cyclic hydrocarbon-selective adsorbent material, and into conduit 236. Hydrogen-rich gas from the cryogenic system flows through conduits 234 and 232, valve 224 and heater 261 to form the hot hydrogen-rich purge gas. The cyclic hydrocarbon-laden hydrocarbon-rich gas in conduit 236 is then merged with the hydrogen feed for the toluene dealkylation system. After the bed containing cyclic hydrocarbon-selective adsorbent, bed 22B, has been fully desorbed, valve 224 is closed and valve 226 is opened to permit a cool hydrogen-rich gas purge of beds 22A and 22B. At the end of this cooling step, the regeneration of adsorption zone 22 is complete and this adsorption zone is now ready to process the feed gas mixture. Bypass for the methane-rich gas and hydrogen-rich gas is provided by conduits 233, valve 229 and by conduit 234 and valve 228, respectively.

The FIG. 3 embodiment is also useful in the case when the hydrogen make-up stream for the toluene dealkylation system contains higher molecular weight aliphatic (paraffinic) hydrocarbons and/or carbon dioxide. Both the vapor phase from the crude benzene separation and the hydrogen feed for the toluene dealkylation unit require water removal but only the former requires cyclic hydrocarbon removal. In the case of heavy hydrocarbons being present in the hydrogen make-up stream for the toluene dealkylation unit, if the streams are combined prior to pretreatment in the adsorption system, co-adsorption and interference by the heavy hydrocarbons can increase cyclic hydrocarbon-selective adsorbent requirements for the cyclic hydrocarbon removal bed by up to 100%. These co-adsorbed hydrocarbons can be recycled to the toluene dealkylation reactor where they react with hydrogen, thereby increasing the hydrogen requirement for the toluene dealkylation reactor above the ideal stoichiometric value. Thus, it is desirable to pass only the toluene dealkylation effluent product gas from the low temperature benzene separation through the bed containing cyclic hydrocarbon-selective adsorbent and to combine the cyclic hydrocarbon-depleted gas with the hydrogen make-up stream prior to passage thereof to the adsorbent bed containing water-selective adsorbent, as in the FIG. 3 embodiment. If carbon dioxide is contained in the make-up hydrogen stream for the toluene dealkylation unit, the methane (aliphatic hydrocarbon)-rich gas purging step of this invention insures that carbon dioxide does not concentrate in the recycle loop to higher levels than can be safely handled.

Figure 4:
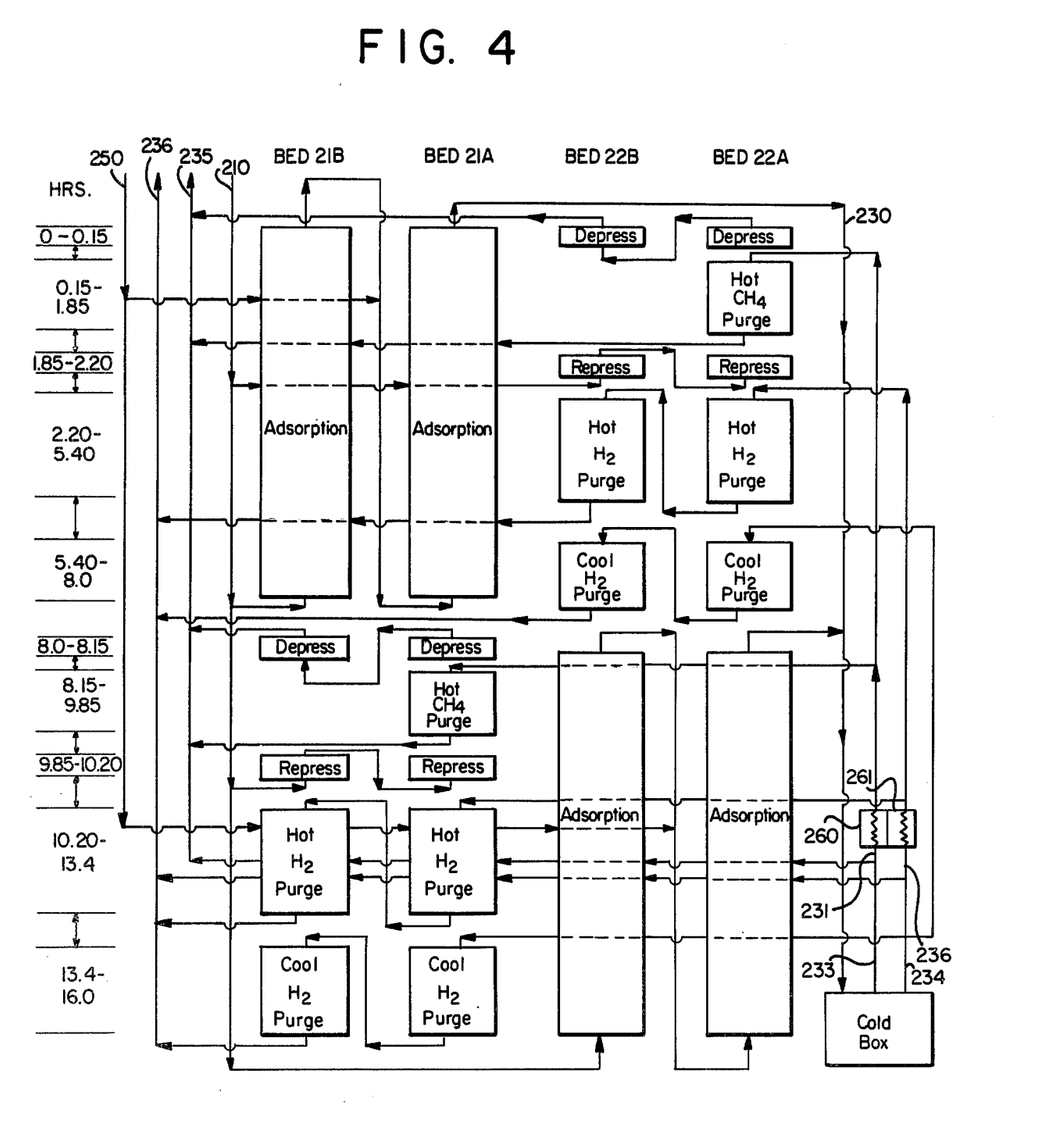
FIG. 4 is a cycle time schedule for the practice of the present invention in the FIG. 3 adsorption system.

FIG. 4 shows a typical time cycle sequence suitable for practice of the instant invention in the adsorption system shown in FIG. 3. The following description will be limited to description of the steps occurring in the adsorption zone 21 consisting of adsorbent beds 21A and 21B; the operation of adsorption zone 22 is 180° out of phase with respect to adsorption zone 21 and, as such, its operation is readily apparent from inspection of the FIG. 4 time cycle diagram.

The time cycle diagram comprises the following steps for the adsorption zone 21:

Step 1 — Time 0–8.0 hours. This first step is an 8 hour adsorption step. Toluene dealkylation effluent gas mixture is subjected to the low temperature benzene separation and the vapor phase recovered from such phase separation is passed through conduit 210 to the inlet end of absorbent bed 21B at a rate of 1,500 lb.-moles/hr. and at a superatmospheric pressure of from 550 to 650 psig. The composition of this stream is shown in Table II below.

TABLE II

| COMPOSITION OF TDA RECYCLE PREPURIFIER FEED | |
|---|---|
| Component | Mole % |
| $H_2$ | 55.0 |
| $CH_4$ | 44.0 |
| $C_2H_6$ | 0.30 |
| $C_6H_6$ | 0.26 |
| $C_7H_8$ | 30 PPM |
| $H_2S$ | 70 PPM |
| $H_2O$ | Saturated |

The methanator off-gas feed stream, the composition of which is shown in Table I herein, is passed through conduit 250 to the inlet end of adsorbent bed 21A at a rate of 3,550 lb.-moles/hr. and at a pressure of 550 to 650 psig where it is mixed with the cyclic hydrocarbon-depleted gas from bed 21B. From adsorbent bed 21A, cyclic hydrocarbon- and water-depleted gas mixture, at a flow rate of 5,500 lb.-mole/hr., is flowed into conduit 230 and thereafter flows to the cryogenic unit, schematically designated as the "cold box."

Step 2 — Time 8.0-8.15 hrs. During this segment of the cycle, beds 21A and 21B are co-currently depressurized. The discharged gas from the adsorption zone is flowed at a flow rate of 350 lb.-moles/hr. into the fuel header conduit 235 as the pressure in adsorption zone 21 is reduced to a first lower pressure of 50-100 psig.

Step 3 — Time 8.15-9.85. This segment of the cycle constitutes a purge step. Methane-rich gas from the cryogenic unit, with a composition as shown in Table III below, flows sequentially through conduits 233 and 231 and is then heated to approximately 450° F. in heater 260. This gas then passes to the feed discharge end of bed 21A at a rate of 350 lb.-moles/hr., and at a pressure of 50-100 psig. The water-containing purge gas discharged from bed 21A then flows into the fuel header conduit 235.

TABLE III

| METHANE-RICH PURGE | |
|---|---|
| Component | Mole % |
| $H_2$ | 4.6 |
| $CH_4$ | 95.0 |
| $C_2H_6$ | 0.3 |

Step 4 — Time 9.85-10.2. This segment of the cycle is a 0.35 hr. repressurization step. Feed gas mixture flows into the feed inlet end of adsorption zone 21 at a rate of 150 lb.-moles/hr., and raises the pressure from the first lower pressure level of 50-100 psig to superatmospheric pressure of 550-650 psig.

Step 5 — Time 10.2-13.4. There follows a 3.2 hr. purge step. Hydrogen-rich gas from the cryogenic unit with a composition as shown in Table IV below flows sequentially through conduit 234 and 232 and is then heated to approximately 450° in heater 261. This gas then flows to the feed discharge end of bed 21A at a rate of 820 lb.-mole/hr. and at superatmospheric pressure of 550-650 psig for sequential flow through adsorbent beds 21A and 21B. In this manner, the hot hydrogen-rich gas is passed through bed 21B containing cyclic hydrocarbon-selective adsorbent wherein the adsorbent has previously been at least partially loaded with cyclic hydrocarbons by passage of gas mixture therethrough. The passage of hot hydrocarbon-rich gas through bed 21B desorbs substantially all of the cyclic hydrocarbons therefrom. The cyclic hydrocarbon-containing purge gas is discharged from bed 21B into hydrogen recycle header 236 for the toluene dealkylation system.

TABLE IV

| HYDROGEN-RICH PURGE | |
|---|---|
| Component | Mole % |
| $H_2$ | 90.0 |
| $CH_4$ | 10.0 |

Step 6 — Time 13.4 to 16.0. This segment of the cycle constitutes a 2.6 hr. cooling step. Cool hydrogen-rich gas flows through conduit 234 to the feed discharge end of bed 21A at a rate of 820 lb.-mole/hr. and at superatmospheric pressure of 550-650 psig for sequential flow through adsorbent beds 21A and 21B. This cooling gas then flows into the hydrogen-recycle header 236 for the toluene dealkylation system.

At the end of the preceding sequence of steps, adsorption zone 21 is fully regenerated and ready to begin processing feed gas mixture while adsorption zone 22 has completed its adsorption step and is ready to be regenerated.

Figure 5:
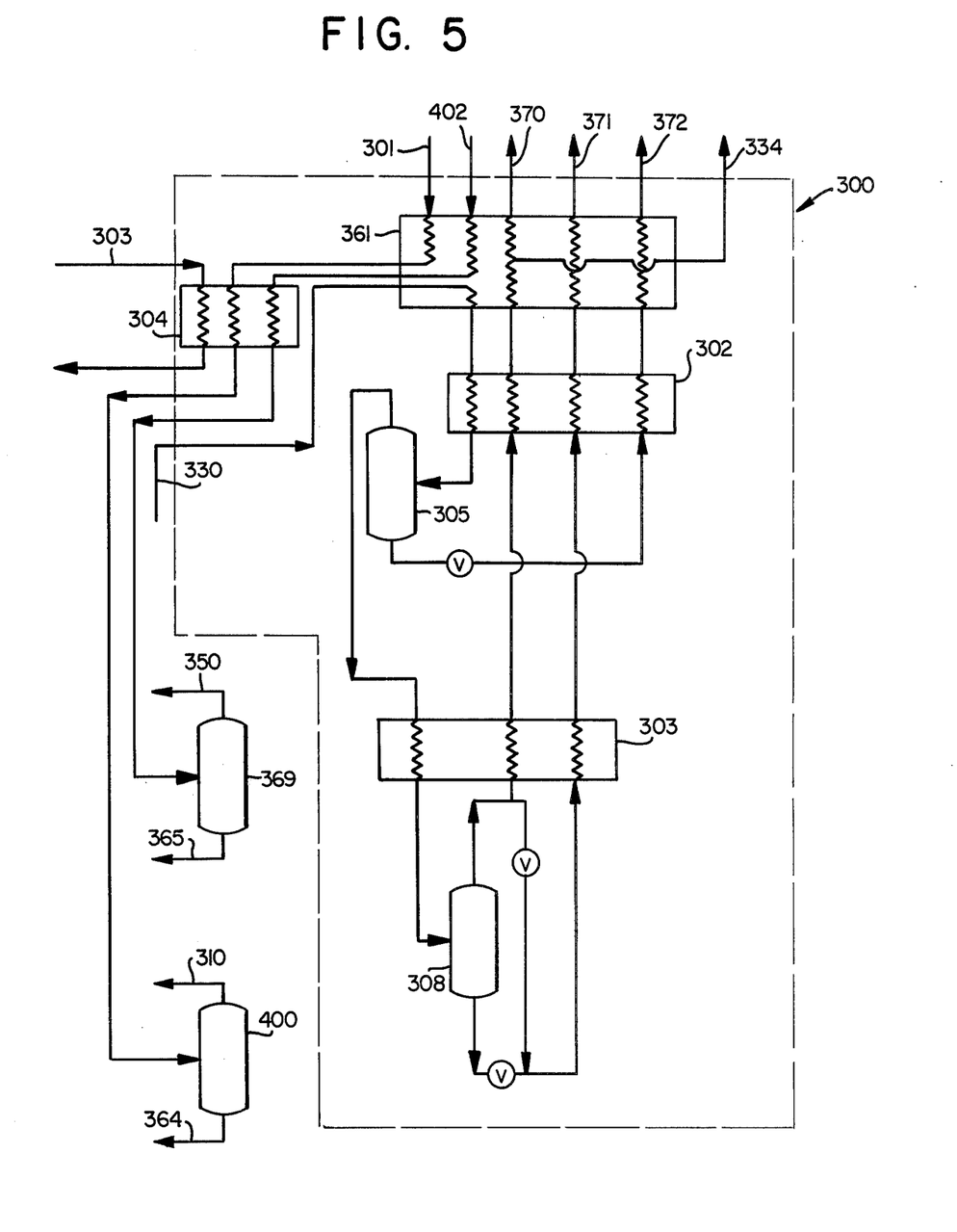
FIG. 5 is a schematic flow sheet of a cyrogenic system such as may be usefully employed in connection with the practice of the present invention.

FIG. 5 illustrates one cryogenic unit 300 which can be used in conjunction with the adsorption prepurifier system of the FIG. 3 and 4 embodiments. The cryogenic unit 300 consists of heat exchangers 361, 302, 303 and 304, phase separators 305 and 308 and the necessary piping and valving. The function of the cryogenic unit 300 is to upgrade hydrogen purity and produce two methane fuel streams of different pressures.

The two feed streams from a toluene dealkylation unit and a methanator flow into the cryogenic unit 300 through conduits 301 and 402 respectively at approximately 110° F. and 600 psig. The two feed streams are separately cooled in the upper section of heat exchanger 361 and chilled further in heat exchanger 304 against a chilled water stream (45° F.) which enters through conduit 303. The chilled feed streams, which are now at approximately 50° F., are sent separately to feed separators 369 and 400, where the bulk of the benzene, toluene and water is removed as liquid condensates through conduits 364 and 365, respectively. The two vapor streams in conduits 310 and 350 are then sent to the adsorption prepurification system of the FIG. 3 embodiment where the remaining condensible contaminants are removed. After prepurification, the combined feed in conduit 330 is then returned to the lower section of heat exchanger 361. The prepurified feed is further cooled and partially condensed in the heat exchanger 302 against the warming hydrogen product stream in conduit 370 and the fuel streams in conduits 371 and 372. The major portion of the methane is separated as a liquid in separator 305, while the vapor stream is further cooled and partially condensed in heat exchanger 303. The resulting two phase mixture is phase separated in separator 308 to produce a vapor hydrogen product of desired purity and a methane-rich liquid stream. The hydrogen product (hydrogen-rich gas) is removed from the cryogenic unit through conduit 370. A portion of the hydrogen-rich gas product is extracted at about the mid-point of heat exchanger 361 through conduit 334 and is subsequently used for the cool hydrogen-rich purge gas for the adsorption system. The liquid from separator 308 is throttled to low pressure e.g., 80 psig, to provide sufficient driving force for heat transfer in heat exchanger 303. A portion of the hydrogen product is mixed with this low pressure fuel stream to promote boiling in heat exchanger 303. After entering heat exchanger 303, the low pressure fuel and the major portion of the hydrogen product from separator 308 are warmed against the feed in the three banks of heat exchangers 303, 302, and 361.

The liquid stream from separator 305 is throttled to fuel. This stream constitutes the higher pressure fuel which is throttled to 100 psig, introduced into heat exchanger 302 and removed from the cryogenic unit 300 in conduit 372. A portion of this stream is subsequently used as the hot methane-rich purge gas in the adsorption system. This stream is warmed against the feed in heat exchangers 302 and 361.

Figure 6:
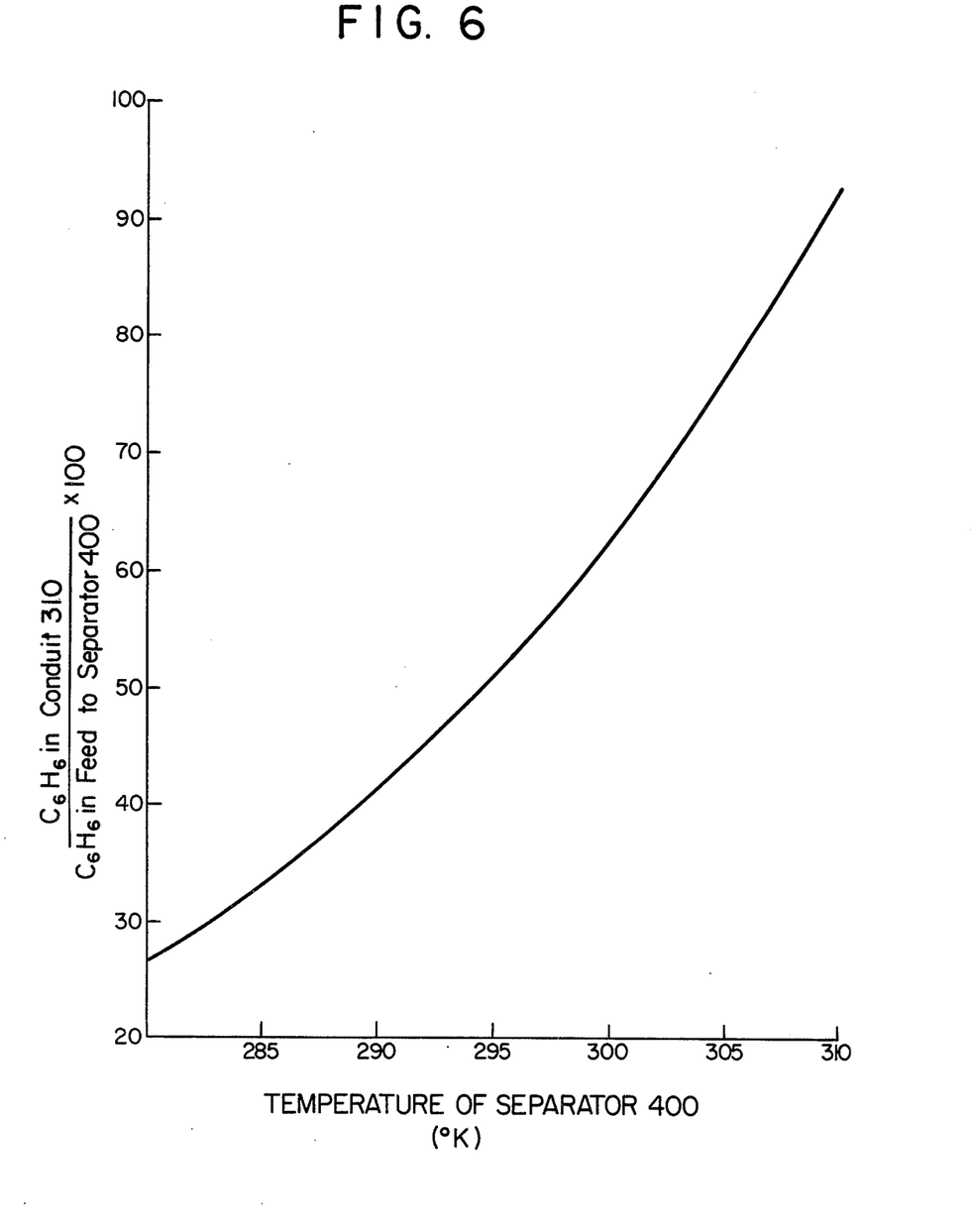
FIG. 6 is a graph of the concentration ratio of benzene in conduit 310 in the FIG. 5 embodiment to benzene in the feed to the separator 400 plotted as a function of temperature in the separator 400.

One advantage of the instant invention not previously discussed will now be described with reference to FIG. 6. This graph represents a plot of the benzene concentration of the vapor fraction recovered from separator 400 in FIG. 5 expressed as a percentage of the benzene concentration of the feed in line 301 to the separator 400, plotted as a function of the temperature of the separator 400. This plot in FIG. 6 is specific to the embodiment of FIGS. 3, 4 and 5, previously discussed, but its general form and characteristics are generally applicable to the process of the instant invention.

In the prior art systems, any adsorbent prepurification unit must employ hot methane regeneration when freezable components other than water are present in any of the cryogenic unit feed streams, to reject such contaminants from the toluene dealkylation loop. Such regeneration, as discussed earlier herein, leads to losses of cyclic hydrocarbons via the fuel gas stream. In connection with FIG. 6, it is seen that the low temperature benzene separation should be operated as close as possible to the freezing point of benzene, in order to minimize the amount of benzene leaving the separator 400 and thereby minimize benzene losses in the adsorption prepurification zone. The prior art systems must operate in a closely controlled manner in order to reduce benzene losses in the methane-rich purge gas. In the process of the present invention, on the other hand, an adsorption method is provided for recovering substantially all of the benzene in the low temperature separation vapor fraction. Thus, the low temperature benzene separation in the present invention can operate at a higher temperature, up to about 100° F., and can thereby avoid the problem of benzene freeze-ups without excessive aromatics losses. In addition, and in connection with such higher temperature operation, the process of the instant invention minimizes the necessary heat exchange area in the heat exchanger 304 or, alternatively, the quantity of chilled water in conduit 303. The temperature in separator 400 should not exceed 100° F. because either the quantity of cyclic hydrocarbon adsorbent becomes excessive or else the cycle time becomes too short for efficient operation.

Figure 7:
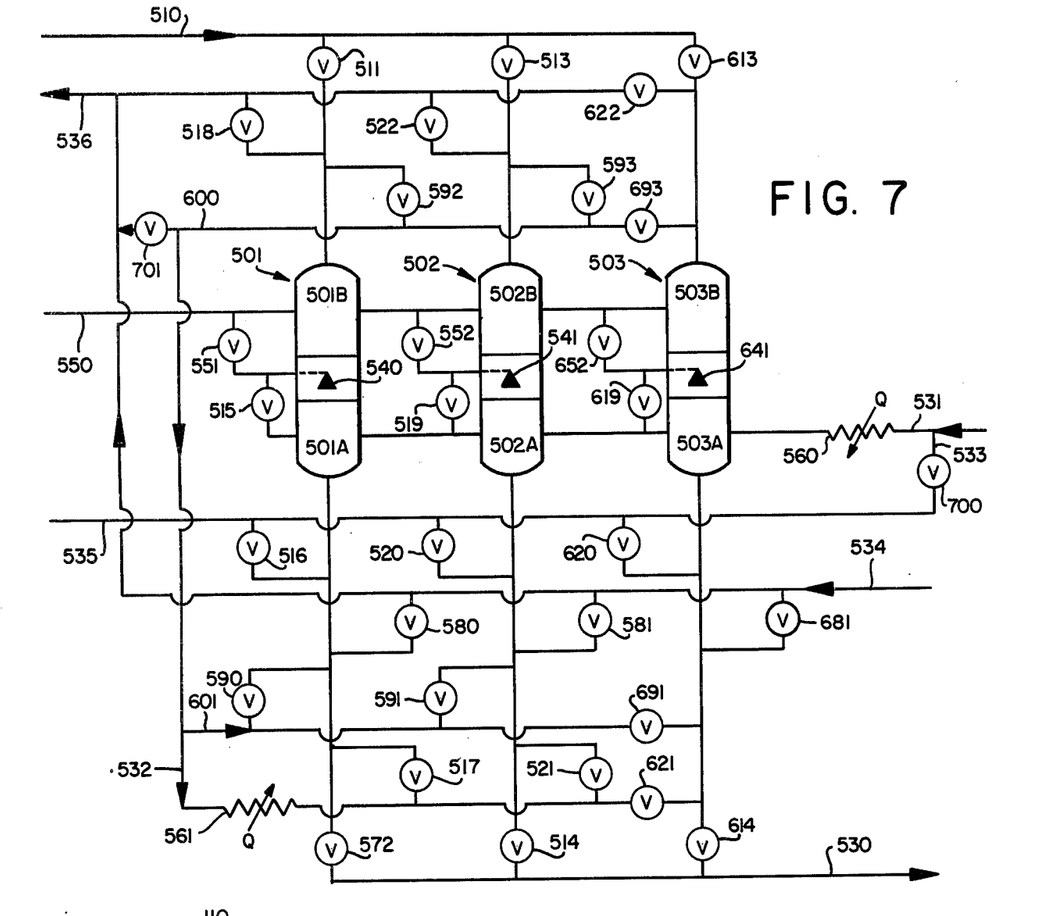
FIG. 7 is a schematic flow sheet of an adsorption system such as may suitably be employed in the practice of the present invention, comprising three adsorption zones each including two adsorbent beds connected in series.

FIG. 7 illustrates an additional embodiment of the present invention wherein three adsorption zones are provided each including two adsorbent beds connected in series, one of the beds containing an adsorbent selective for cyclic hydrocarbons and the other bed containing an adsorbent selective for water. The system will be described below with adsorption zone 501 on the adsorption portion of the cycle, adsorption zone 502 on the desorption portion of the cycle, and adsorption zone 503 on the cooling portion of the cycle. This three adsorption zone system is employed in a continuous cyclic process wherein each adsorption zone undergoes the successive steps of adsorption, desorption and cooling.

Feed gas mixture at superatmospheric pressure containing hydrogen methane, water and cyclic hydrocarbons flows through conduit 510 and valve 511 into adsorption zone 501. Adsorption zone 501 consists of beds connected in series, one of the adsorbent beds containing as adsorbent selective for hydrocarbons, bed 501B, and the other bed, bed 501A, containing an adsorbent selective for water. In the same manner beds 502B and 503B of adsorption zones 502 and 503 respectively contain an adsorbent material selective for cyclic hydrocarbons, while bds 502A and 503A contain adsorbent selective for water. The feed gas mixture in conduit 510 first passes through bed 501B for removal of cyclic hydrocarbons therein. Subsequently, prior to passage through bed 501A, the cyclic hydrocarbon-depleted stream is mixed with an additional water-containing feed stream, which may for example comprise the hydrogen make-up stream for the toluene dealkylation unit, which enters through conduit 550 and valve 551 and fluid distribution device 540. The resulting combined feed stream passes through bed 501A for water removal therein and is discharged from bed 501A through valve 572 into conduit 530 as prepurified feed gas mixture for the cryogenic unit (not shown). Since adsorption zone 501 is on the adsorption step of the cycle, valves 515, 516, 517, 518, 580, 590 and 592, which are associated with the desorption and cooling portions of the cycle for adsorption zone 501, are closed.

While the adsorption zone 501 is processing feed gas mixture for prepurification thereof, adsorption zone 502 is undergoing desorption, as part of its regeneration sequence. Prior to the desorption of adsorption zone 502, valves 513, 552 and 514, which are associated with the adsorption portion of the cycle for adsorption zone 502, are closed. Additionally, valves 581 and 593, which are employed in the cooling step of the regeneration sequence for adsorption zone 502 are also closed. The adsorption zone 502 is first co-currently depressurized to first lower pressure by opening valve 520 and allowing the gaseous contents of adsorption zone 502 to slowly bleed into the fuel header conduit 535. When the depressurization step is complete, valve 519 is opened to allow hot methane-rich gas to flow co-currently through adsorbent bed 502A, thereby desorbing the major portion of the adsorbed components (water) therefrom. The methane-rich gas, from the cryogenic unit, flows through conduit 531 and heating means 560 to form the hot methane-rich purge gas. During the periods when hot methane-rich purge gas is not required for desorption of the adsorbent beds containing water-selective adsorbent, valve 700 may suitably be opened so that methane-rich gas from the cryogenic unit is diverted in line 533 to fuel header conduit 535. At the termination of the hot methane-rich purging step, when substantially all of the water is desorbed from adsorbent bed 502A, valves 519 and 520 are closed and adsorption zone 502 is countercurrently repressurized with cool hydrogen-rich gas. The cool hydrogen-rich gas employed for repressurization comprises the gas used previously for the cooling of adsorption zone 503, as described more fully hereinbelow. The cooling gas flows through conduits 600 and 601 and open valve 591 into adsorption zone 502. When repressurization is complete, valve 591 is closed and valves 521 and 522 are opened to permit a countercurrent hot hydrogen-rich gas purging of adsorption zone 502. A portion of the cool hydrogen-rich gas from the cooling of adsorption zone 503, to be described more fully hereinafter, flows through conduits 600 and 532 and is heated by heating means 561. This heated gas stream then passes through the open valve 521, through adsorption zone 502, thereby desorbing the cyclic hydrocarbons previously adsorbed in bed 502B, and is discharged through the open valve 522 into the hydrogen-rich gas manifold conduit 536. The hydrogen-rich gas in conduit 536 is subsequently recycled to the toluene dealkylation reactor. While adsorption zones 501 and 502 are respectively undergoing the adsorption and desorption portions of the cyclic process, the adsorption zone 503 is undergoing the cooling portion of the cycle. Valves 681 and 693 are opened while those valves associated with the adsorption and desorption of adsorption zone 503 remain closed. Cool hydrogen-rich gas derived from the cryogenic unit flows through conduit 534 and valve 681 for the countercurrent cooling of adsorption zone 503. The cool hydrogen-rich gas is then discharged from adsorption zone 503 through valve 693 into conduit 600. A portion of this gas is subsequently used for the repressurization and hot purging of adsorption zone 502, as described hereinabove. Any portion of the hydrogen-rich gas not employed in the regeneration step for adsorption zone 502 flows to the hydrogen-rich gas manifold conduit 536 through valve 701. Although various apparatus elements shown in the FIG. 7 drawing have not been described in detail in the foregoing discussion, it will be apparent that the use of such elements is analogous to those specifically described. The correspondence according to which the undescribed system elements are analogous to elements already described is as follows: fluid distribution devices 541 and 641 correspond to fluid distribution device 540; valve 613 corresponds to valves 511 and 513; valve 614 corresponds to valves 572 and 514; valve 619 corresponds to valves 515 and 519; valve 620 corresponds to valves 516 and 520; valve 621 corresponds to valves 517 and 511; valve 622 corresponds to valves 518 and 522; valve 652 corresponds to valves 551 and 552; and valve 619 corresponds to valves 590 and 591.

Figure 8:
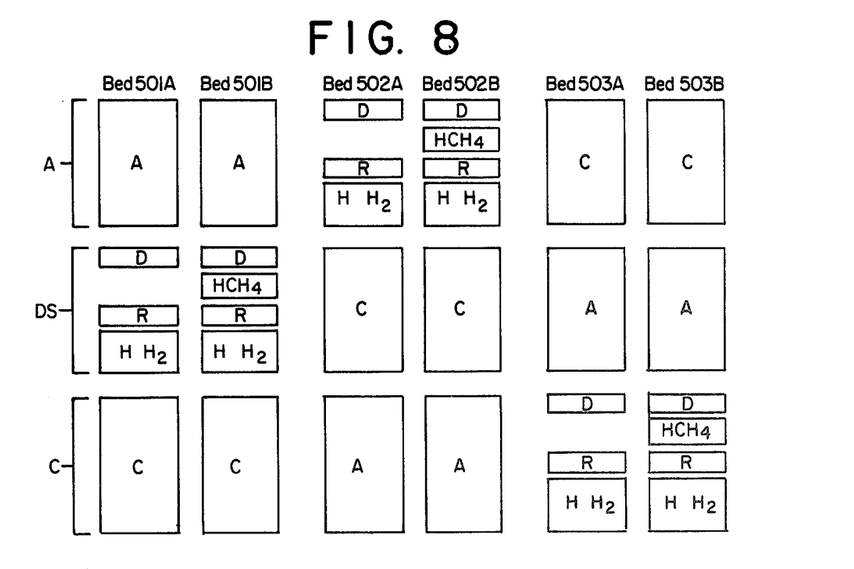
FIG. 8 is a process cycle step diagram of a process according to the present invention such as may be usefully employed in the FIG. 7 adsorption system.

FIG. 8 shows a time cycle diagram such as may suitably be employed to carry out the previously described process in the FIG. 7 adsorption system. As illustrated, the overall process consists of three primary steps, adsorption, designated on the left-hand side by "A," desorption, designated on the left-hand side by "DS," and cooling designated on the left-hand side by "C." It will be seen from the diagram that while adsorption zone 501 is on adsorption, adsorption zone 502 is on desorption and adsorption zone 503 is on cooling. Subsequently, while adsorption zone 501 undergoes desorption, adsorption zone 502 is on cooling and adsorption zone 503 is on adsorption. Finally, while adsorption zone 501 undergoes cooling, adsorption zone 502 is on adsorption and adsorption zone 503 is on desorption. Each of the three described portions of the cycle may for example comprise a 6 hr step, controlled by appropriate time cycle devices as is well known to those skilled in the art. As also shown, the desorption portion of the cycle is further divided into a depressurization (D) step, a hot methane-rich gas purge (HCH4) step, a repressurization (R) step and a hot hydrogen-rich gas purge (HH2) step. These steps in the desorption portion of the cycle may for example comprise a 9 minute step for depressurization, a one hour and 45 minutes step for hot methane-rich gas purging, a 30 minute repressurization step and a 3 hour and 36 minute hot hydrogen-rich gas purge step. It will be seen that each of the adsorbent beds in a given adsorption zone undergoes the same portions of the cycle simultaneously and that the operation of the respective adsorption zones is staggered so that at any given time one adsorption zone is on the adsorption step to provide a continuous flow of cyclic hydrocarbon-and water-depleted gas mixture as feed to the cryogenic unit.

Although preferred embodiments of the invention have been described in detail, it will be appreciated that other embodiments are contemplated only with modifications of the disclosed features, as being within the scope of the invention.

What is claimed is:

1. A process for separation of water and cyclic hydrocarbons from a gas mixture containing hydrogen, methane and said water and cyclic hydrocarbons, comprising:
   (a) providing an adsorption zone including two adsorbent beds connected in series, one of said beds containing an adsorbent selective for cyclic hydrocarbons and the other bed containing an adsorbent selective for water;
   (b) sequentially passing said gas mixture through the adsorbent beds for preferential adsorption therein of cyclic hydrocarbons and water and discharging cyclic hydrocarbon-and water-depleted gas mixture from said adsorption zone;
   (c) heating hydrogen-rich gas substantially free of cyclic hydrocarbons as purge gas and passing same through the bed containing cyclic hydrocarbon-selective adsorbent having previously been at least partially loaded with cyclic hydrocarbons by passage of said gas mixture therethrough, thereby desorbing substantially all of the cyclic hydrocarbons and discharging cyclic hydrocarbon-containing purge gas therefrom;
   (d) heating an aliphatic hydrocarbon-rich gas substantially free of water as purge gas and passing same through the bed containing water-selective adsorbent having previously been at least partially loaded with water by passage of said gas mixture therethrough, thereby desorbing substantially all of the water and discharging water-containing purge gas therefrom; and
   (e) cooling the desorbed adsorbent beds of steps (c) and (d), for subsequent passage of said gas mixture therethrough in the manner of step (b).

2. A process according to claim 1 wherein said cyclic hydrocarbon-and water-depleted gas mixture discharged from said adsorption zone is separated into hydrogen-rich gas and methane-rich gas, with the hydrogen-rich gas being employed as said purge gas in step (c) and the methane-rich gas being employed as said purge gas in step (d).

3. A process according to claim 2 wherein said cyclic hydrocarbon-and water-depleted gas mixture discharged from said adsorption zone is cryogenically separated into hydrogen-rich gas and methane-rich gas, by the steps of: cooling said cyclic-hydrocarbon-and water-depleted gas mixture to condense a methane-rich liquid fraction; separating said methane-rich liquid fraction from the uncondensed hydrogen-rich gas; and vaporizing said methane-rich liquid fraction to form said methane-rich gas by heat exchange with said cyclic hydrocarbon-and water-depleted gas mixture as part of said cooling of the latter.

4. A process according to claim 3 wherein said uncondensed hydrogen-rich gas is rewarmed prior to said heating in step (c) by heat exchange with said cyclic hydrocarbon-and water-depleted gas mixture as another part of said cooling of the latter.

5. A process according to claim 1 wherein said aliphatic hydrocarbon-rich gas is substantially pure in a component selected from the group consisting of methane, ethane and propane.

6. A process according to claim 1 wherein said adsorbent selective for cyclic hydrocarbons is selected from the group consisting of silica gel and activated carbon.

7. A process according to claim 1 wherein said adsorbent selective for water is selected from the group consisting of 4A, 5A and 13X molecular sieve and alumina.

8. A process according to claim 1 wherein said gas mixture also contains hydrogen sulfide and wherein the bed containing water-selective adsorbent is disposed first in series, upstream of the bed containing cyclic hydrocarbon-selective adsorbent.

9. A process according to claim 1 wherein the bed containing cyclic hydrocarbon-selective adsorbent is disposed first in series, upstream of the bed containing water-selective adsorbent.

10. A process according to claim 9 wherein another gas mixture containing hydrogen, water and paraffinic hydrocarbons is passed through the adsorbent bed containing water-selective adsorbent together with said gas mixture in step (b).

11. A process according to claim 10 wherein said another gas mixture is passed through only the adsorbent bed containing water-selective adsorbent together with said gas mixture in step (b).

12. A process for separation of water and cyclic hydrocarbons from a gas mixture containing hydrogen, methane and said water and cyclic hydrocarbons, comprising:
(a) providing at least two adsorption zones each including two adsorbent beds connected in series, one of said beds containing an adsorbent selective for cyclic hydrocarbons and the other bed containing an adsorbent selective for water;
(b) sequentially passing said gas mixture through the adsorbent beds in a first adsorption zone for preferential adsorption therein of cyclic hydrocarbons and water and discharging cyclic hydrocarbon-and water-depleted gas mixture from said first adsorption zone;
(c) heating a hydrogen-rich gas substantially free of cyclic hydrocarbons as purge gas and passing same through the bed containing cyclic hydrocarbon-selective adsorbent in an other-than-first adsorption zone having previously been at least partially loaded with cyclic hydrocarbons by passage of said gas mixture therethrough, thereby desorbing substantially all of the cyclic hydrocarbons and discharging cyclic hydrocarbon-containing purge gas therefrom;
(d) heating an aliphatic hydrocarbon-rich gas substantially free of water as purge gas and passing same through the bed containing water-selective adsorbent in an other-than-first adsorption zone having previously been at least partially loaded with water by passage of said gas mixture therethrough, thereby desorbing substantially all of the water and discharging water-containing purge gas therefrom; and
(e) cooling the desorbed adsorbent beds of steps (c) and (d), for subsequent passage of said feed gas mixture therethrough in the manner of step (b).

13. A process according to claim 12 wherein the passage of said gas mixture through the adsorbent beds of said first adsorption zone is terminated following at least partial loading of the bed containing hydrocarbon-selective adsorbent with cyclic hydrocarbons and at least partial loading of the bed containing water-selective adsorbent with water; hydrogen-rich gas substantially free of cyclic hydrocarbons is heated as purge gas and passed through the bed containing cyclic hydrocarbon-selective adsorbent in said first adsorption zone, thereby desorbing substantially all of the cyclic hydrocarbons, and cyclic hydrocarbon-containing purge gas is discharged therefrom; aliphatic hydrocarbon-rich gas substantially free of water is heated as purge gas and passed through the bed containing water-selective adsorbent in said first adsorption zone, thereby desorbing substantially all of the water, water-containing purge gas is discharged therefrom; and the desorbed adsorbent beds in said first adsorption zone are cooled, for subsequent passage of said gas mixture therethrough.

14. A process according to claim 13 wherein the following steps are sequentially conducted in each of the adsorption zones: passing said gas mixture through the adsorbent beds of said adsorption zone; terminating the passage of said gas mixture following at least partial loading of the bed containing hydrocarbon-selective adsorbent with cyclic hydrocarbons and at least partial loading of the bed containing water-selective adsorbent with water; heating aliphatic hydrocarbon-rich gas substantially free of water as purge gas and passing same through the bed containing water-selective adsorbent in said adsorption zone, thereby desorbing substantially all of the water, and discharging water-containing purge gas therefrom; heating hydrogen-rich gas substantially free of cyclic hydrocarbons as purge gas and passing same through the bed containing cyclic hydrocarbon-selective adsorbent in said adsorption zone, thereby desorbing substantially all of the cyclic hydrocarbons, and discharging cyclic hydrocarbon-containing purge gas therefrom; and cooling the desorbed adsorbent beds in said adsorption zone, for subsequent passage of said gas mixture therethrough.

15. A process according to claim 14 wherein said aliphatic hydrocarbon-rich purge gas is passed through only the bed containing water-selective adsorbent.

16. A process according to claim 14 wherein the preferential adsorption of water in the bed containing water-selective adsorbent is conducted at superatmospheric pressure above the pressure of said aliphatic hydrocarbon-rich purge gas, wherein following the termination of the gas mixture passage through the adsorbent beds in the adsorption zone, gas is released from the bed containing water-selective adsorbent for depressurization from said superatmospheric pressure to the pressure of said aliphatic hydrocarbon-rich purge gas and wherein following the purging of the bed containing water-selective adsorbent, said bed is repressurized to said superatmospheric pressure.

17. A process according to claim 1 wherein said gas mixture contains benzene and the temperature of said gas mixture is below about 100° F. and above the freezing point of benzene in said gas mixture.

18. A process for separation of water and cyclic hydrocarbons from a gas mixture at superatmospheric pressure containing hydrogen, methane and said water and cyclic hydrocarbons, comprising:
(a) providing two adsorption zones each including two adsorbent beds connected in series, one of said beds containing an adsorbent selective for cyclic hydrocarbons and the other bed containing an adsorbent selective for water;
(b) sequentially passing said gas mixture at superatmospheric pressure through the absorbent beds in a first adsorption zone for preferential adsorption therein of cyclic hydrocarbons and water and discharging cyclic hydrocarbon-and water-depleted gas mixture from said first adsorption zone;
(c) separating the cyclic hydrocarbon-and water-depleted gas mixture into hydrogen-rich gas and methane-rich gas;
(d) depressurizing the adsorbent beds in the second adsorption zone through which said gas mixture at superatmospheric pressure has previously been passed for preferential adsorption therein of cyclic hydrocarbons and water, from said superatmospheric pressure to a first lower pressure;

(e) heating a portion of said methane-rich gas as purge gas and passing same at said first lower pressure through the depressurized bed containing water-selective adsorbent in the second adsorption zone, having previously been at least partially loaded with water by passage of said gas mixture therethrough, thereby desorbing substantially all of the water and discharging water-containing purge gas therefrom;

(f) repressurizing the adsorbent beds in said second adsorption zone to said superatmospheric pressure;

(g) heating a portion of said hydrogen-rich gas as purge gas and passing same at said superatmospheric pressure through the bed containing cyclic hydrocarbon-selective adsorbent in the second adsorption zone having previously been at least partially loaded with cyclic hydrocarbons by passage of said gas mixture therethrough, thereby desorbing substantially all of the cyclic hydrocarbons and discharging cyclic hydrocarbon-containing purge gas therefrom; and (h) cooling the desorbed adsorbent beds of steps (e) and (g), for subsequent passage of said gas mixture therethrough in the manner of step (b).

19. A process for separation of water and cyclic hydrocarbons from a gas mixture at superatmospheric pressure containing hydrogen, methane and said water and cyclic hydrocarbons, comprising:

(a) providing three adsorption zones each including two adsorbent beds connected in series, one of said beds containing an adsorbent selective for cyclic hydrocarbons and the other bed containing an adsorbent selective for water;

(b) sequentially passing said gas mixture at superatmospheric pressure through the absorbent beds in a first adsorption zone for preferential adsorption therein of cyclic hydrocarbons and water and discharging cyclic hydrocarbon-and water-sepleted gas mixture from said first adsorption zone;

(c) separating the cyclic hydrocarbon-and water-depleted gas mixture into hydrogen-rich gas and methane-rich gas;

(d) depressurizing the adsorbent beds in a second adsorption zone through which said gas mixture at superatmospheric pressure has previously been passed for preferential adsorption therein of cyclic hydrocarbons and water, from said superatmospheric pressure to a first lower pressure;

(e) heating a portion of said methane-rich gas as purge gas and passing same at said first lower pressure through the depressurized bed containing water-selective adsorbent in the second adsorption zone having previously been at least partially loaded with water by passage of said gas mixture therethrough, thereby desorbing substantially all of the water and discharging water-containing purge gas therefrom;

(f) repressurizing the adsorbent beds in said second adsorption zone to said superatmospheric pressure;

(g) heating a portion of said hydrogen-rich gas as purge gas and passing same at said superatmospheric pressure through the bed containing cyclic hydrocarbon-selective adsorbent in the second adsorption zone having previously been at least partially loaded with cyclic hydrocarbons by passage of said gas mixture therethrough, thereby desorbing substantially all of the cyclic hydrocarbons and discharging cyclic hydrocarbon-containing purge gas therefrom; and (h) cooling the adsorbent beds in the third adsorption zone having previously been at least partially loaded with water and cyclic hydrocarbons by passage of said gas mixture therethrough and thereafter desorbed of substantially all of the water and cyclic hydrocarbons in the manner of steps (e) and (g).

* * * * *